United States Patent
Safadi et al.

(10) Patent No.: US 6,752,997 B2
(45) Date of Patent: Jun. 22, 2004

(54) PROCESS FOR PREPARING NON-HYGROSCOPIC SODIUM VALPROATE COMPOSITION

(75) Inventors: Mohammed S. Safadi, Nazareth (IL); Maya Barder, Haifa (IL); Yechiel Golander, Haifa (IL); Avraham Yacobi, Englewood, NJ (US); Daniel A. Moros, Larchmont, NY (US); Barrie Levitt, Mamaroneck, NY (US); Michael Friedman, Jerusalem (IL)

(73) Assignee: Taro Pharmaceuticals U.S.A., Inc., Hawthorne, NY (US)

(*) Notice: Subject to any disclaimer, the term of this patent is extended or adjusted under 35 U.S.C. 154(b) by 0 days.

(21) Appl. No.: 10/057,155

(22) Filed: Jan. 24, 2002

(65) Prior Publication Data

US 2003/0119872 A1 Jun. 26, 2003

Related U.S. Application Data

(63) Continuation-in-part of application No. 09/767,853, filed on Jan. 24, 2001, now abandoned.

(51) Int. Cl.$^7$ ................................................ A61K 9/00
(52) U.S. Cl. ...................... 424/400; 424/401; 424/451; 424/452; 424/464
(58) Field of Search ................................. 424/400, 401, 424/451, 452, 464

(56) References Cited

U.S. PATENT DOCUMENTS

| | | | |
|---|---|---|---|
| 4,301,176 A | 11/1981 | Grabowski | 424/318 |
| 4,772,540 A | 9/1988 | Deutsch et al. | 430/320 |
| 4,913,906 A | 4/1990 | Friedman et al. | 424/499 |
| 4,988,731 A | 1/1991 | Meade | 514/557 |
| 5,017,613 A | 5/1991 | Aubert et al. | 514/557 |
| 5,049,586 A | 9/1991 | Ortega et al. | 514/557 |
| 5,055,306 A * | 10/1991 | Barry et al. | 424/482 |
| 5,185,159 A * | 2/1993 | Aubert et al. | 424/489 |
| 5,212,326 A | 5/1993 | Meade | 562/606 |
| 5,589,191 A | 12/1996 | Ukigaya et al. | 424/480 |
| 5,707,663 A | 1/1998 | Ayer et al. | 424/473 |

FOREIGN PATENT DOCUMENTS

| | | | |
|---|---|---|---|
| EP | 133110 | 2/1985 | |
| EP | 0 442 012 | 8/1991 | A61K/31/20 |
| EP | 0 571 973 | 12/1993 | A61K/31/20 |

OTHER PUBLICATIONS

A. Kibbe, "Calcium Phosphate, Dibasic Dihydrate," *Handbook of Pharmaceutical Excipients*, pp. 63–67.
A. Kibbe, "Cellulose, Microcrystalline," *Pharmaceutical Excipients*, pp. 102–105.
M. O'Neill, "Calcium Silicate," *The Merck Index–13th Edition*, p. 284 (2001).
Hasegawa et al., "Inhibition of the Moisture Absorption of Sodium Valproate by Organic Acid," *Yakuzaigaku* 47(2): 86092 (1987), and English language abstract.

* cited by examiner

*Primary Examiner*—José Dees
*Assistant Examiner*—Konata M. George
(74) *Attorney, Agent, or Firm*—Darby & Darby

(57) ABSTRACT

The invention is directed to non-hygroscopic oral pharmaceutical compositions of a salt of valproic acid, and processes for preparing the compositions. The non-hygroscopic pharmaceutical compositions are prepared by blending a hygroscopic salt of valproic acid, carbomer, and a non-hygroscopic additive.

55 Claims, No Drawings

PROCESS FOR PREPARING NON-HYGROSCOPIC SODIUM VALPROATE COMPOSITION

This application is a continuation-in-part of U.S. patent application Ser. No. 09/767,853, filed Jan. 24, 2001 now abandoned, which is hereby incorporated by reference herein.

FIELD OF THE INVENTION

This invention is directed to pharmaceutical compositions (including dosage forms) of a salt of valproic acid that (despite the hygroscopicity of the active ingredient) resists absorbing moisture from the environment and hence remains stable over a prolonged period of time. The invention encompasses the compositions, processes for producing the compositions, and methods of treating medical conditions using the compositions.

BACKGROUND OF THE INVENTION

Valproic acid and its pharmaceutically acceptable salts are useful for treating various forms of epilepsy as well as certain other disorders. Valproic acid is considered a first line therapy for treating petit mal, monoclonic seizures, generalized and partial motor seizures, absence and infantile spasms. Recently, valproic acid was also approved for the treatment of partial epilepsy, bipolar disorders (psychotic disorders) and migraine.

The effective blood concentrations of the drug generally range from 50 to 100 mg/ml. Because valproate salts, such as sodium valproate, have a short biological half life, the drug usually needs to be administered more than once (e.g. three times a day) to maintain an effective blood concentration. Since such a short dose interval reduces patient compliance, there have been many efforts to develop sustained release preparations of sodium valproate.

Although valproic acid or its salts have known utility as anti-convulsants, a number of problems are associated in formulating them in a solid form. According to the Merck Index, valproic acid is a liquid and therefore suffers from the difficulties attendant any liquid formulation; that is, it is inconvenient to use since the precise volume necessary to result in administration of the proper dose must be measured for each administration, and it is less easily portable than solid dosage forms. Efforts have been made to address the problems of administering valproic acid by converting it to its salt forms, which are solid. However, as disclosed in U.S. Pat. No. 4,301,176, the sodium salt of valproic acid is hygroscopic. Hygroscopicity interferes with and, in fact, has precluded production of a compressed tablet formulation, and thus is a serious disadvantage.

Various attempts have been made to formulate moisture-stable solid valproic acid and valproic acid salt formulations. U.S. Pat. No. 5,049,586 discloses conventional (immediate-release) formulations of valproic acid containing fillers, disintegrants, binders and lubricants. The lubricated granulate disclosed therein is said to be a dry, non-hygroscopic mixture which is said to be suitable for use in forming compressed tablets or for filling capsules. The formulation is asserted to be moisture stable and to need no protective coating. However, production of the tablets described in the '586 patent is disadvantageous because the production requires a wet granulation step and is more complicated compared to the procedure described in the present invention.

U.S. Pat. Nos. 5,017,613 and 5,185,159 disclose a pharmaceutical composition based on valproic acid and one of the pharmaceutically acceptable salts in the absence of any binder. According to the '613 and '159 patents, the granules for compression are formed directly by simply mixing with a suitable granulating solvent. Valproic acid is added slowly, either directly or by spraying, to the valproic acid salt, with the granular agglomeration occurring automatically in a few minutes. The granules thus obtained were passed through a screen for calibration. This operation could be carried out in an atmosphere of 55–60% relative humidity, without risk of any uptake of moisture. The compressibility of these granules was found to be very good and, moreover, the valproic acid acted as a lubricant.

Similarly EP 0 133 110 discloses an oral tablet pharmaceutical composition of approximately 25–35% by weight of valproic acid and about 65–75% by weight of sodium valproate. The granules for compression are formed directly by mixing suitable proportions of valproic acid and one of the pharmaceutically acceptable salts thereof in the absence of any binder or granulating solvent.

U.S. Pat. Nos. 4,988,731 and 5,212,326 disclose a highly stable non-hygroscopic, solid entity prepared from valproic acid and its salts, which is a single crystalline entity consisting of one molecule each of valproic acid or diethylacetic acid and sodium valproate salt. It was shown that the crystalline compound has equal or better physiological properties than either valproic acid or sodium valproate. Since the crystalline compound has far superior physical characteristics than either monomer from which it is made, it greatly facilitates the preparation of solid pharmaceutical dosage forms.

The methods disclosed in U.S. Pat. Nos. 5,017,613, 5,185,159, 4,988,731, 5,212,326 and EP 0 133 110 are disadvantageous since these methods require reaction between valproic acid and its salt to produce a new entity. Moreover the production of the new entity, according to U.S. Pat. Nos. 4,988,731 and 5,212,326, includes steps involving cooling and filtration which complicates the production of the new formed entity.

The production of the granules according to U.S. Pat. Nos. 5,017,613, 5,185,159 and EP 0 133 110 is disadvantageous. Since valproic acid is a viscous liquid which is hard to handle and the granules for compression are formed in the absence of a granulating solvent, this may lead to a technological difficulty in forming an homogeneous mixture of valproic acid and valproic acid salt.

Hasegawa et al. [Hasegawa, A. et al., *YAKUZAIGAKU*, 47: 86–92, 1987] describes a solid dispersion of water insoluble carriers and sodium valproate. This composition inhibits moisture absorption when a saturated fatty acid such as stearic acid or other organic acids such as citric acid, succinic acid or tartaric acid are employed. Although it was shown that these solid dispersions inhibit moisture uptake, such compositions are disadvantageous since relatively high concentrations of the acids are required (about 20% by weight of sodium valproate). Moreover, part of these reactions (especially the reaction with citric acid) are exothermic and require cooling of the mixture. In particular, the reaction of sodium valproate with citric acid is highly exothermic and leads to melting of the mixture, which is a serious disadvantage.

Other attempts have been made to develop controlled release pharmaceutical compositions of valproic acid and its salts and other derivatives. U.S. Pat. No. 4,913,906 discloses a controlled release dosage form of valproic acid, sodium valproate, valproamide and other derivatives of therapeutic value. The controlled release oral dosage form comprises a homogeneous admixture of an active ingredient and a physiologically acceptable polymer or a native protein. Although the formulations described were found to provide sustained release action, the production of the tablets requires that such dosage form should be performed in dry atmosphere cabinet, at less than 30% Relative Humidity (RH) which is a serious disadvantage, especially for commercial scale products.

None of these prior art references disclose a process for preparing a non-hygroscopic composition of a salt of valproic acid which can be produced under a variety of relative humidity conditions (including RH substantially higher than 30%) by combining a hygroscopic salt of valproic acid with a polymeric agent and a non-hygroscopic additive.

There is a widely recognized need for an effective formulation containing a solid valproic acid derivative, which is non-hygroscopic, simple to produce, lower in cost and yet suitable for treatment of epilepsy, psychotic disorders and migraine headaches as described in the present invention. There is an acute need for such a formulation that is a sustained release and/or an enteric coated formulation.

SUMMARY OF THE INVENTION

This invention is directed to processes for preparing pharmaceutical compositions comprising as an active ingredient a hygroscopic salt of valproic acid in an effective amount comprising the step of intimately mixing (i) said hygroscopic salt; (ii) a carbomer and (iii) a non-hygroscopic additive to form a homogeneous mixture; wherein the amount of said carbomer and said non-hygroscopic additive are sufficient relative to the amount of said hygroscopic salt to produce, said mixture having the following property: when compressed into tablets, said tablets do not absorb more than 5% water by weight after being stored for 3 months at 75% relative humidity.

The invention is also directed to non-hygroscopic oral pharmaceutical compositions comprising a pharmaceutically effective amount of a hygroscopic salt of valproic acid, a carbomer, and a non-hygroscopic additive, wherein the amount of said carbomer and said non-hygroscopic additive are sufficient relative to the amount of said hygroscopic salt to produce, said compositions having the following property: not absorbing more than 5% by weight water after being stored for 3 months at 75% relative humidity.

The invention is further directed to non-hygroscopic oral pharmaceutical compositions comprising a pharmaceutically effective amount of a hygroscopic salt of valproic acid, a carbomer, and a non-hygroscopic additive, wherein the amount of said carbomer and said non-hygroscopic additive are sufficient relative to the amount of said hygroscopic salt to produce, said compositions having the following property: when compressed into tablets, said tablets not absorbing more than 5% by weight water after being stored for 3 months at 75% relative humidity.

The invention also includes a method of treating a medical condition in a human patient, the method comprising the step of orally administering non-hygroscopic highly stable pharmaceutical compositions for release of a salt of valproic acid into the bloodstream at a physiologically effective level, wherein said compositions comprise a pharmaceutically effective amount of a hygroscopic salt of valproic acid, a carrier, a non-hygroscopic additive, and wherein the weight ratio of the carbomer to the hygroscopic salt of valproic acid is from about 1:3 to about 1:10 and the weight ratio of the non-hygroscopic additive to the hygroscopic salt of valproic acid is from about 1:6 to about 1:2.

DETAILED DESCRIPTION OF THE INVENTION

A "hygroscopic" material is a material that readily absorbs water (usually from the atmosphere).

A "non-hygroscopic" composition is intended to mean a composition which absorbs less than 5% moisture and preferably less than 2% of its weight. It is a usual practice to test hygroscopicity at RH 75% by exposing the material to be tested to these RH conditions for three months.

The active ingredient of the present invention is a salt of valproic acid. Although the preferred salt is sodium valproate, any other hygroscopic salt or derivative of valproic acid that is suitable for oral administration, or mixtures of valproic acid salts and derivatives can be used.

The processes for preparing a non-hygroscopic oral pharmaceutical composition of a salt of valproic acid includes the step of intimately mixing the active ingredient, i.e., a hygroscopic salt of valproic acid, a carbomer, and a non-hygroscopic additive to form a homogenous mixture. The amounts of the carbomer and the non-hygroscopic additive are sufficient relative to the amount of the hygroscopic salt so that the composition itself (or tablets made from it) does not absorb more than 5% water after being stored for 3 months at 75% relative humidity. The homogeneity of the mixture is determined by any means known for that purpose, including by testing the uniformity of dissolution of several tablets made from this mixture, or by assaying for the quantity of active ingredient contained in the tablets, or both. Surprisingly, the homogeneous mixture may be prepared in relative humidities of greater than 30 percent. The resulting composition, when compressed into tablets, does not absorb more than 5% water after being stored for 3 months at 75% relative humidity. Alternatively, the mixture can be tested in the same manner as powder or granulate without tableting, and be found to absorb no more than 5% water after being stored for three months.

A "sufficient amount" is that amount needed to obtain the desired result, i.e., a mixture, which itself or when compressed into tablets, is non-hygroscopic.

In one embodiment of the invention, the weight ratio of the carbomer to the hygroscopic salt of valproic acid (C/V) is from about 1:3 to about 1:100, preferably from about 1:3 to about 1:10, and the weight ratio of the non-hygroscopic additive to the hygroscopic salt of valproic acid (A/V) is from about 1:6 to about 1:2.

Sustained release properties are achieved in formulations containing a ratio of carbomer to active ingredient of at least 1:6 and preferably at least 1:10 within the aforementioned broad range.

A preferred embodiment of the process includes an additional step of adding at least one excipient to the mixture containing the hygroscopic salt of valproic acid, carbomer and non-hygroscopic additive.

A further embodiment of the process includes further compressing the ingredients into a solid dosage form after the step of intimately mixing (e.g. by blending) to form a homogenous mixture. The time of mixing depends on several factors, including the ratios of (C/V) and (A/V), and the amount of carbomer. Generally, the present compositions can be mixed into homogeneous mixtures by blending for a few minutes due to the relatively high amount of the active ingredient. If any ingredient is present in a very small amount, the mixing time would be longer in order to assure homogeneity with respect to the low-amount ingredient, since homogeneity with respect to all ingredients is preferred. In any event, the mixing must occur for a period of time which is sufficient to obtain a homogenous mixture. In some embodiments, the time of mixing may be about five minutes or less.

For purposes of this specification and the accompanying claims, the phrase "closed conditions" indicates that the experiment was done in a closed container such as a bottle.

The pharmaceutical composition remains non-hygroscopic under relative humidity of from about 30% to about 75% at 40° C. in closed conditions and more preferably from about 30% to about 60% at 25° C. in closed conditions, when the carbomer is present in an amount such that the weight ratio of carbomer to sodium valproate is in the range of from about 1:3 to about 1:100, preferably about 1:3 to about 1:10 and the weight ratio of non-hygroscopic additive to sodium valproate is in the range of from about 1:6 to about 1:2.

The compositions of the present invention may be prepared as solid dosage forms such as bulk powders, tablets, caplets, pellets, capsules, sachets, granules, and any other dosage form suitable for oral administration. For purposes of this specification and the accompanying claims, the term "tablet" refers equally to a tablet, a caplet or any other solid dosage form which is suitable for oral administration.

Preferably, the solid dosage form contains from about 50 to about 1200 mg of a salt of valproic acid or derivative, and more preferably, from about 100 to about 650 mg.

Preferably, the derivative of valproic acid is present in an amount from about 5% to about 99% of the weight of the final composition, more preferably from about 10% to about 90%, and most preferably from about 40% to about 65% of the weight of the final composition. As long as the composition contains at least 1/100 as much carbomer as the active ingredient, the non-hygroscopic property will be observed provided that the amount of additive is commensurating increased in order to make a composition that does not have a disproportionate amount of active ingredient. For example, if the composition contains 1 gram of carbomer and 100 grams of valproate, it should contain about 90 grams of additive. Preferably, however, the amount of carbomer will not be as low as in this example. See preferred C/V ratio range above.

A carbomer is a synthetic high molecular weight cross-linked polymer of acrylic acid. Carbomers are hydroxylated vinylic polymers referred to as "interpolymers" which are prepared by crosslinking a monoolefinic acrylic acid monomer with a polyalkyl ether of sucrose. Any carbomer which is pharmaceutically acceptable for oral administration may be used. Preferred polymers are lightly crosslinked carboxy-polymethylenes available as Carbopol™ 971P and Carbopol™ 71G from the B.F. Goodrich Chemical Company of Charlotte, N.C.

In contrast to expectations, it is the "three-way" combination of carbomer with a non-hygroscopic additive that prevents the liquefaction of salts of valproic acid due to moisture or water absorption. The combination of carbomer alone with the active ingredient is not enough to prevent the liquefaction of the active ingredient, and furthermore does not form an acceptable composition for compressing into a tablet. However, the three-way combination of carbomer and a non-hygroscopic additive with the active ingredient yields a finished composition that does not absorb significant amounts of water. Without being held to a particular theory, the inventors believe that the non-hygroscopic additive and carbomer synergize to achieve this effect. Additionally, the additive imparts good flow properties to the composition which are necessary for the compression into tablets. No adjustment in pH, by the addition of acids or bases, is necessary to stabilize the composition. It is especially noteworthy that from the point of view of achieving non-hygroscopic properties, a small amount of carbomer is effective, as long as it is used in the three-way combination, as described herein.

Carbomer also serves as a dissolution retarding agent of the composition, thereby enabling the formation of a non-hygroscopic composition of the active ingredient. Carbomer can be mixed with the active ingredient in regulated amounts to attain the desired drug release characteristics.

The term "sustained release" is used in its conventional sense to refer to a drug formulation that provides for gradual release of a drug over an extended period of time, substantially exceeding the half life of the active ingredient if administered in a non-sustained (e.g. instantaneous) release formulation. Preferably, although not necessarily, sustained release administration results in substantially constant blood levels of a drug over an extended time period.

Preferably, a single dose of the solid dosage form contains from about 6 mg to about 400 mg of carbomer and more preferably from about 50 mg to about 250 mg of carbomer.

Preferably, carbomer is present in an amount of from about 0.2% to about 30% of the weight of the final composition and more preferably from about 0.2% to about 20% of the weight of the final composition. The amount of carbomer present in a sustained release form of the composition ranges from about 5 to about 15% of the weight of the final composition, and more preferably from about 6 to about 10% of the weight of the composition. It is to be understood that the "final composition" may include additional optional ingredients. It is also understood that the ratios of the three key ingredients should be within at least the broad ranges of C/V and A/V given above.

Preferably, carbomer is present in an amount such that the weight ratio of carbomer to active ingredient is in the range of from about 1:3 to about 1:100, preferably about 1:3 to about 1:10.

The non-hygroscopic additive is used in the present invention to enhance the non-hygroscopic properties of the composition. The non-hygroscopic additive is any material which assists in preventing the moisture absorption of the salt of valproic acid and retains the non-hygroscopic properties of the composition. It is believed that the non-hygroscopic additive helps delay and prevent water from getting to the active ingredient of the composition while giving the composition optimum flow properties. The preferred ratio of non-hygroscopic additive to active ingredient is within the range of 1:6 to 1:2. The non-hygroscopic additives include, but are not limited to, dibasic calcium phosphate anhydrous, calcium silicate, microcrystalline cellulose or mixtures thereof. Preferably, a single dose of the solid dosage form contains from about 90 mg to about 400 mg of non-hygroscopic additive.

The non-hygroscopic additive is present in an amount of from about 10% to about 40% of the weight of the final composition and more preferably from about 15% to about 35% of the weight of the final composition. Again, the weight ratio ranges given above should be adhered to.

A preferred non-hygroscopic additive is dibasic calcium phosphate anhydrous. Dibasic calcium phosphate anhydrous is a non hygroscopic ingredient which does not pick up significant moisture over a wide range of relative humidities. Dibasic calcium phosphate anhydrous serves also as a direct compression agent when the bulk powder is further processed into compression tablets. Calcium silicate is most preferred. The mixtures according to the invention are highly compressible, thereby resulting in tablets with excellent physical properties.

Preferably, the non-hygroscopic additive is present in an amount such that the weight ratio of the non-hygroscopic additive to the carbomer is in the range of from about 2:1 to about 35:1.

The features of a compressed tablet of the invention include the active ingredient, a carbomer, a non-hygroscopic additive, and optionally at least one additional excipient. The additional excipients include pharmaceutical lubricants, binders, disintegrators, glidants, adsorbents, and mixtures thereof. The excipients give the desired flow of the granules, prevent the adhesion of material to the punches and dies, modify the dissolution profile, improve the non-hygroscopic properties of the tablets and provide the desired compressibility properties of the composition. A moisture barrier coating is preferably included instead of or in addition to any other coatings of the tableted dosage form.

Binders are agents used to impart cohesive qualities to the powdered material. Binders impart a cohesiveness to the tablet formulation which insures the tablet remains intact after compression, and improves the free-flowing qualities by the formulation of granules of desired hardness and size. Suitable binder materials include, but are not limited to, starch (including corn starch and pregelatinzed starch), gelatin, sugars (including sucrose, glucose, dextrose, lactose and sorbitol), polyethylene glycol, waxes, natural and synthetic gums, e.g., acacia, tragacanth, sodium alginate, celluloses, and Veegum, and synthetic polymers such as polymethacrylates and polyvinylpyrrolidone.

Lubricants have a number of function in tablet manufacture. They prevent adhesion of the tablet material to the surface of the dies and punches, reduce interparticle friction, facilitate the ejection of the tablets from the die cavity and may improve the rate of flow of the tablet granulation. Examples of suitable lubricants include, but are not limited to, magnesium stearate, calcium stearate, stearic acid, glyceryl behenate, talc, sodium lauryl sulfate, sodium stearyl fumarate, polyethylene glycol or mixtures thereof. A preferred lubricant herein is magnesium stearate.

Preferably, the lubricant is present in an amount from about 0.25% to about 5% of the weight of the final composition and more preferably from about 0.5 to about 1.5% of the weight of the final composition.

A disintegrant is a substance, or a mixture of substances, added to a tablet to facilitate its breakup or disintegration after administration. Materials serving as disintegrants have been classified chemically as starches, clay, celluloses, aligns, gums and cross-linked polymers. Examples of suitable disintegrants include, but are not limited to, crosscarmelose sodium, sodium starch glycolate, starch, magnesium aluminum silicate, colloidal silicon dioxide, methylcellulose, agar, bentonite, alginic acid, guar gum, citrus pulp, carboxymethyl cellulose, microcrystalline cellulose, or mixtures thereof. A preferred disintegrant is sodium starch glycolate.

Preferably, the disintegrator is present in an amount from about 0.5% to about 25% of the weight of the final composition and more preferably from about 1% to about 15% of the weight of the final composition.

Glidants are substances which improve the flow characteristics of a powder mixture. Examples of glidants include, but are not limited to colloidal silicon dioxide, talc or mixtures thereof.

Preferably, the glidant is present in an amount of from about 0.1% to about 10% of the weight of the final composition and more preferably from 5 about 0.1% to about 5% of the weight of the final composition.

The adsorbent may be, for example colloidal silicon dioxide, microcrystalline cellulose, calcium silicate or mixtures thereof.

Preferably, the adsorbent is present in an amount from about 0.05% to about 42% of the weight of the final composition and more preferably from about 0.05% to about 37% of the weight of the final composition.

If desired, other ingredients, such as diluents, stabilizers and antiadherants, which are conventionally used for pharmaceutical formulations, may be included in the present formulations.

Optional ingredients include coloring and flavoring agents which are well known in the art.

The present invention further provides a non-hygroscopic orally deliverable pharmaceutical composition containing as an active ingredient a salt of valproic acid or other solid derivative thereof in an effective amount, (i.e., an amount resulting in the release into the bloodstream of effective levels of valproic acid), the composition including a pharmaceutically effective amount of a hygroscopic derivative of valpoic acid, a carbomer, a non-hygroscopic additive, and at least one excipient.

Although the preferred salt is sodium valproate, any other hygroscopic salt or derivative of valproic acid that is suitable for oral administration, or mixtures of valproic acid salts and derivatives can be used.

Any carbomer which is pharmaceutically acceptable for oral administration may be used. A particularly preferred polymer is a lightly crosslinked carboxypolymethylene available as Carbopol™ 971P and Carbopol™ 71G from the B.F. Goodrich Chemical Company of Charlotte, N.C. Preferably, carbomer is present in an amount from about 0.2% to about 30% of the weight of the final composition and more preferably from about 0.2% to about 20% of the weight of the final composition. The amount of carbomer present in a sustained release form of the composition ranges from about 5 to about 15% of the weight of the final composition, and more preferably from about 6 to about 10% of the weight of the composition.

The non-hygroscopic additive may be, preferably, dibasic calcium phosphate anhydrous, calcium silicate, microcrystalline cellulose or mixtures thereof and more preferably dibasic calcium phosphate anhydrous or calcium silicate. The non-hygroscopic additive is present in an amount ranging from about 10% to about 40% and preferably from about 15% to about 35%.

The present invention further provides a method of treating a medical condition in a human patient, the method including the step of orally administering a non-hygroscopic highly stable pharmaceutical composition for release of a salt of valproic acid into the bloodstream at a physiologically effective level, wherein the composition includes a pharmaceutically effective amount of a hygroscopic salt of valproic acid, a carrier, a non-hygroscopic additive, and at least one excipient.

The terms "effective amount" or "therapeutically effective amount" of an active agent as provided herein is defined as an amount of the agent at least sufficient to provide the desired therapeutic effect. (Preferably, nontoxic levels of the active agent will be employed, if possible.) The exact amount required will vary from subject to subject, depending on age, general condition of the subject, the severity of the condition being treated, and the particular active agent administered, and the like.

The medical condition treated with the present formulation may be, for example, epilepsy, a psychotic disorder or a migraine headache.

The pharmaceutical composition described in the present invention is formulated to release active ingredient in a sustained release or an immediate release manner. The in vitro and in vivo drug release profile depends mainly on the carbomer.

Sustained release compositions can be formulated such that, in vitro, preferably from about 5% to about 40% of the active ingredient is released after 2 hours, preferably from about 10% to about 50% is released after 6 hours, approximately from about 30% to about 90% is released after 8 hours and approximately from about 50% to about 100% is released within 12 to 24 hours.

Immediate release compositions can be formulated such that in vitro approximately 70% of the drug is released in one hour.

Enteric coated compositions are coated with a coating that withstands the low pH conditions of the upper gastric tract but dissolves in the intestines. Enteric coated composition may be released or sustained release compositions (after dissolution of the coating).

The pharmaceutical composition may be, for example, in the form of a tablet, a caplet, a pellet, a capsule, a granule, a tablet which disintegrates into granules, a pill, a powder or a sachet. Preferably the pharmaceutical composition is in the form of a tablet or a caplet, more preferably the caplet is oval shaped. The capsule may contain a powder, a compressed powder or a granule.

The pharmaceutical compositions of the present invention are administered orally.

The pharmaceutical composition may further be coated with a moisture barrier film, to further improve the non-hygroscopic properties of the composition. Suitable moisture barrier coatings comprise aqueous solutions of polyvinyl alcohol. Indeed, it is a tribute to the present composition that it so well protects the active ingredient from absorbing moisture that tablets can be coated with an aqueous solution. Other moisture barrier coatings can also be used, e.g., steatic acid, wax, etc.

The process for preparing non-hygroscopic, highly moisture stable composition of sodium valproate need not be carried in a "dry room" but may be practiced at a relative humidity of from about higher than 30% and up to about 75%. It is, however, preferred that the RH be controlled, but only so that it not exceed about 50%.

The amount of sodium valproate in the formulation varies depending on the desired dose for efficient drug delivery. The actual amount of the used drug is dependent on the patient's age, weight, sex, disease and on any other medical criteria, and is determined according to intended medical use by techniques known in the art. The pharmaceutical dosage forms of the invention may be administered once or more times per day, as determined by the attending physician, and as warranted by the release profile of the composition.

Typically, to treat seizure disorders, sodium valproate is formulated in a tablet or other dosage form in amounts of 10–40 mg/kg body weight per day, preferably 15–30 mg/kg body weight per day. For adults, the daily dose is typically 20 mg/kg body weight per day. For children and infants, the daily dose is typically 25 mg/kg body weight per day.

When a sustained release dosage form is to be administered, the daily dosage of sodium valproate or other solid derivative of valproate acid is formulated in a sustained release composition to be released slowly to maintain therapeutic levels of sodium valproate in patients blood between about 50 to about 100 µg/ml. Above this concentration, patients may experience adverse effects.

The daily dose can be formulated in a single tablet, or more than one tablet, depending on the daily dose of the valproate salt, the final weight of the composition and the number of times the formulation is to be administered.

It is to be understood that the invention is not limited in its application to the details of construction and the arrangement of the components set forth in the following description. The invention includes other embodiments and can be practiced or implemented in various ways. Also it is to be understood that the phraseology and terminology employed herein is for the purpose of description only and should not be regarded as limiting.

DEFINITIONS

For purposes of this specification and the accompanying claims, the term "Cab-O-Sil®" refers to colloidal silicon dioxide or aerosil available from Cabot Corporation of Boston, Mass.

For purposes of this specification and the accompanying claims, the term "A-tab®" refers to dibasic calcium phosphate anhydrous or dibasic calcium phosphate available from Rhone-Poulenc, Monmouth Junction, N.J.

For purposes of this specification and the accompanying claims, the term "Explotab®" refers to sodium starch glycolate available from Edward Mendell Co. of Carmel, N.Y.

For purposes of this specification and the accompanying claims, the term "Avicel®" refers to microcrystalline cellulose available from FMC Corporation of Philadelphia, Pa.

For purposes of this specification and the accompanying claims, the term "Ac-Di-Sol®" refers to crosscarmelose sodium available from FMC Corporation of Philadelphia, Pa.

EXAMPLES

Reference is now made to the following examples, which together with the above descriptions, illustrate the invention in a non limiting fashion.

Generally, the nomenclature used herein and the laboratory procedures in the pharmaceutical technology described below are those well known and commonly employed in the art. Standard techniques are used for tablet preparation and drug release measurement. Generally tablet preparation is performed using the direct compression method. Measurement of drug release from the tablet is performed using the USP basket method 1. These techniques and various other techniques are generally performed according to The United States Pharmacopoeia XXI, pp. 1243–1244, 1985; A. Osol (Ed.) Remington's Pharmaceutical Sciences, 16tb Edition, Tablets Capsules and Pills, pp. 1553–1584, 1980.

Various formulations of sodium valproate according to the present invention were prepared as specified in the Examples given below.

The formulation of the following examples were prepared using the following method.

(a) Sodium valproate, CARBOPOL® 971 carbomer, and non-hygroscopic additives are admixed and blended in V-blender for about 5 minutes;

(b) the blend from step (a) is comminuted through a 0.250" screen;

(c) the mixture from step (b) is passed through 20 mesh vibrating sieve;

(d) the sifted material from step (c) is blended in a V-blender for an additional 15 minutes;

(e) magnesium stearate is passed through a 50-mesh sieve;

(f) the sieved magnesium stearate from step (e) is added to the resulting granulate from step (d) and blended for 5 minutes; and (g) the blend from step (f) is compressed into caplets.

Example 1

Sodium valproate (576 mg) tablets were prepared using various combinations of additional materials as described hereinabove and detailed in Tables I, II, III, IV and V. The values in parenthesis present the percentage of the ingredient based on the total weight of the caplet (% w/w).

TABLE I

| Ingredient | RD-D-0276 mg/tablet (% w/w) | RD-0293 mg/tablet (%, w/w) | RD-0294 mg/tablet (%, w/w) | RD-0296 mg/tablet (%, w/w) | RD-0297 mg/tablet (%, w/w) | RD-0314 mg/tablet (%, w/w) |
|---|---|---|---|---|---|---|
| sodium valproate | 576 (56.14%) | 576 (56.14%) | 576 (56.14%) | 576 (56.14%) | 576 (65.56%) | 576 56.14%) |
| Cab-O-Sil | 20 (1.95%) | 15 (1.46%) | 15 (1.46%) | 20 (1.95%) | 15 (1.71%) | 20 (1.95%) |
| A-tab | 266 (25.93%) | 324.5 (31.63%) | 343 (33.43%) | 297 (28.95%) | 193 (21.96%) | 358 (34.89%) |
| Carbomer 971P | 154 (15.01%) | 100.5 (9.80%) | 82 (8.00%) | 123 (11.99%) | 86 (9.79%) | 62 (6.04%) |
| Mg Stearate | 10 (0.97%) | 10 (0.97%) | 10 (0.97%) | 10 (0.97%) | 8.6 (0.98%) | 10 (0.98%) |

TABLE II

| Ingredient | RD-0315 mg/tablet (%, w/w) | RD-316 mg/tablet (%, w/w) | RD-0331 mg/tablet (%, w/w) | RD-0332 mg/tablet (%, w/w) | RD-0334 mg/tablet (%, w/w) | RD-0335 mg/tablet (%, w/w) |
|---|---|---|---|---|---|---|
| Sodium Valproate | 576 (64.00%) | 576 (62.61%) | 576 (55.85%) | 576 (56.14%) | 576 (55.82%) | 576 (58.78%) |
| Cab-O-Sil | 20 (2.22%) | 9.6 (4.30%) | 20 (1.94%) | 20 (1.95%) | 10 (0.97%) | 10 (1.02%) |
| A-Tab | 241 (26.78%) | 240 (26.09%) | 358 (34.71%) | 337.9 (32.93%) | 338 (32.75%) | 92.9 (29.89%) |
| Carbomer 971P | 54 (6.00%) | 55.2 (6.00%) | 62 (6.01%) | 82.1 (8.00) | 82.4 (7.99%) | 78.4 (8.00%) |
| Talc | — | — | — | — | 10 (0.97%) | 8 (0.81%) |
| Mg Stearate | 9 (1.00%) | 9.2 (1.00%) | 15.4 (1.49%) | 10 (0.98%) | 15.5 (1.50%) | 14.7 (1.50%) |

TABLE III

| Ingredient | RD-0336 mg/table (%, w/w) | RD-0340 mg/tablet (%, w/w) | RD-0341 mg/tablet (%, w/w) | RD-0342 mg/tablet (%, w/w) | RD-0343 mg/tablet (%, w/w) |
|---|---|---|---|---|---|
| Sodium Valproate | 576 (58.78%) | 576 (58.78%) | 576 (58.78%) | 576 (58.78%) | 576 (58.78%) |
| Carbomer 971 P | 78.4 (8.00%) | 68.6 (7.00%) | 58.8 (6.00%) | 93.1 (9.50%) | 8.8 (6.00%) |
| Cab-O-Sil | 0 (1.02%) | 0 (1.02%) | 0 (1.02%) | 0 (1.02%) | 0 (1.02%) |
| Talc | (0.81%) | (0.81%) | (0.81%) | (0.81%) | (0.81%) |
| A-Tab | 292.9 (29.89%) | 302.7 (30.89%) | 312.5 (31.89%) | 278.2 (28.39%) | 273.3 ((27.89%) |
| Explotab | — | — | — | — | 39.2 (4.00%) |
| Mg Stearate | 14.7 (1.50%) | 14.7 (1.50%) | 14.7 (1.50%) | 14.7 (1.50%) | 14.7 (1.50%) |

TABLE IV

| Ingredient | RD-0419 mg/tablet (%, w/w) | RD-376 mg/tablet (%, w/w) | RD-0393 mg/tablet (%, w/w) |
|---|---|---|---|
| Sodium Valproate | 576 (57.27%) | 576 (52.36%) | 576 (56.47%) |
| Carbomer 971P | 2 (0.20%) | 20 (1.82%) | 5 (0.49%) |
| Avicel PHI 12 | 187 (18.59%) | — | — |
| A-Tab | — | 169 (15.36%) | 164 (16.08%) |
| Calcium Silicate | 80 (7.95%) | 200 (18.18%) | 160 (15.69%) |
| Ac-Di-Sol | 140 (13.92%) | 110 (10.00%) | — |
| Starch 1500 (Source) | — | — | 100 (9.80%) |
| Talc (Source) | — | 10 (0.91%) | — |
| Mg. Stearate | 20.8 (2.07%) | 15 (1.37%) | 15 (1.47%) |

TABLE V

| Ingredient | B.N.780277 mg/tablet (%, w/w) | B.N.780278 mg/tablet (%, w/w) | B.N.780279 mg/tablet (%, w/w) | B.N.780280 mg/tablet (%, w/w) |
|---|---|---|---|---|
| Sodium Valproate | 576 (58.78%) | 576 (58.78%) | 576 (58.78%) | 576 (58.78%) |
| Carbomer 971 P | 58.8 (6.00%) | 93.1 (9.50%) | 78.4 (8.00%) | 68.6 (7.00%) |
| Cab-O-Sil | 10 (1.02%) | 10 (1.02%) | 10 (1.02%) | 10 (1.02%) |
| Talc | 8 (0.81%) | 8 (0.81%) | 8 (0.81%) | 8 (0.81%) |
| A-tab | 312.5 (31.89%) | 278.2 (28.39%) | 292.9 (29.89%) | 302.7 (30.89%) |
| Mg Stearate | 14.7 (1.50%) | 14.7 (1.50%) | 14.7 (1.50%) | 14.7 (1.50%) |

TABLE V-continued

| Ingredient | B.N.780277 mg/tablet (%, w/w) | B.N.780278 mg/tablet (%, w/w) | B.N.780279 mg/tablet (%, w/w) | B.N.780280 mg/tablet (%, w/w) |
|---|---|---|---|---|
| % Relative Humidity | | | | |
| Blending Stage | 40–43% | 29–42% | 26–42% | 41–44% |
| Packaging Stage | 44–48% | 46–48% | — | 46–48% |

All the formulations presented in Tables I–V may optionally be coated using the Pan Method with an anti-moisture barrier, for example aqueous Opadry AMB (Colorcon, England).

The tablets described in Table V are representative of the formulations presented in Tables I–IV. The formulations were non-hygroscopic during all stages of tablet preparation. The blend did not uptake moisture under relative humidity of 30–50%. The final tablets had very good physical properties and exhibited excellent hardness and friability as presented in table VI.

TABLE VI

Finished product physical properties.

| Friability | Hardness (Kp) | % Carbomer | Batch No. |
|---|---|---|---|
| 0.08% | 19.09 | 7% | 780280 |
| 0.043% | 20.8 | 8% | 780279 |
| 0.027% | 20.57 | 9.5% | 780278 |
| 0.05% | 19.12 | 6% | 780277 |

The formulations presented in Table V demonstrate that the combination of sodium valproate, carbomer and dibasic calcium phosphate anhydrous prevents the liquefaction of sodium valproate and forms non-hygroscopic highly stable dosage forms.

The formulations described in Table V were packaged in 200 ml HDPE white bottles containing 100 tablets each with 3 Sorb-It-Can Desiccants added to each bottle. The bottles contained a polypropylene safety cap and a heat seal aluminum liner. One kg of tablets, made according to the formulations described in Table V, were also packaged in double polyethylene bags with desiccant in between the two layers. The polyethylene bags were then placed in a plastic container. The desiccant was added so that the tablets were placed under conditions similar to products that would be placed on the shelves of pharmacies and dispensed to patients.

The amount of moisture absorbed by the tablets was measured after 3 months at room temperature. The batches were also tested at one, two and three month intervals under accelerated conditions at 40° C. and 75% relative humidity. The results are shown in Table VII.

TABLE VII

Stability test results of loss on drying for 100.Tablets/Pack and bulk containers(*)

| B.N. | 0M | 1M Acc[a] | 2M Acc | 3M Acc | 3M RT | 1M RT Bulk[b] | 3M RT Bulk |
|---|---|---|---|---|---|---|---|
| 780277 | 0.3% | 0.2% | 0.23% | 0.2% | 0.3% | 0.2% | 0.2% |
| 780280 | 0.3% | 0.2% | 0.18% | 0.2% | 0.2% | 0.2% | 0.2% |
| 780279 | 0.2% | 0.1% | 0.15% | 0.2% | 0.2% | 0.2% | 0.6% |
| 780278 | 0.3% | 0.1% | 0.16% | 0.2% | 0.2% | 02% | 0.6% |

[a]Accelerated stability
[b]Bulk containers

The results presented in table VII show that the finished product (tablets) is non-hygroscopic. The final products have excellent physical properties as indicated by the loss on drying test which was unchanged during the stability period.
(*) Specifications
Loss on drying: Not more than 2.0%
Package Type for 100 tablets: 200 mLHDPE white bottle, Polypropylene safety cap,
Heat Seal Aluminum liner.
Desiccant type: 3 Sorb-It-Can Desiccants containing 1 g each.
Package type for 1 Kg of tablets per pack bulk: double polyethylene bag with desiccant in between two layers placed in a plastic container.

Example 3

Sodium Valproate Release Kinetics of Formulations as Assayed by the Dissolution Studies Four of the formulations described in Table III, RD-0336, RD-00341, RD-0340 and RD-0342, were tested as follows.

The dissolution kinetics of tablets of the formulations were monitored using a commercially available tablet dissolution tester (Vankel VK7000 with sampler VK8000 available from Varian of Cary, N.C.). The USP basket method I [The United States Pharmacopoeia XXI, pp. 1243–1244, 1985] was used. Rotation speed was 100 rpm. The dissolution profile was examined in 900 ml buffer pH 2.0 USP for 3 hours after which the medium was exchanged to 900 ml phosphate buffer pH 6.8 for an additional 5 hours. The dissolution medium was maintained at 37±0.5° C. The dissolution studies were performed using 12 tablets for each composition tested. Results are summarized in tables VIII and IX.

At specified time intervals samples were taken from the dissolution medium and sodium valproate levels were monitored using HPLC. The following conditions were used for HPLC analysis of sodium valproate:

| | |
|---|---|
| Instrument: | Suitable chromatograph with a variable wavelength UV detector (BPI 100 or Waters Alliance) |
| Column | |
| Manufacturer's name: | Hypersil Elite |
| Type: | C18 |
| Dimensions: | 150 × 2.1 mm |
| Particle size: | 5 pm |
| Detection: | UV at 220 nm |
| Flow rate: | 0.3 mL/min |
| Injection volume: | 20 pL |
| Run time: | 6 minutes |
| Mobile Phase: | 45:55 Buffer pH 3/Acetonitrile |

TABLE VII

Sodium Valproate Release Kinetics

Amount Released (%)

| Time (hrs) | RD0336 (8% Carbomer) | RD0341 (6% Carbomer) | RD0340 (7% Carbomer) | RD0342 (9.5% Carbomer) |
|---|---|---|---|---|
| 0 | 0 | 0 | 0 | 0 |
| 1 | 23 | 31 | 27 | 20 |
| 2 | 33 | 43 | 37 | 28 |
| 3 | 40 | 50 | 45 | 34 |
| 4 | 48 | 63 | 55 | 42 |
| 5 | 55 | 71 | 63 | 48 |
| 6 | 60 | 77 | 69 | 54 |
| 7 | 65 | 81 | 74 | 59 |
| 8 | 70 | 85 | 78 | 64 |

TABLE IX

Sodium valproate release kinetics

Amount Released (%)

| Time (hrs) | 780280 (7% Carbomer) | 780279 (8% Carbomer) | 780278 (9.5% Carbomer) | 780277 (6% Carbomer) |
|---|---|---|---|---|
| 0 | 0 | 0 | 0 | 0 |
| 1 | 27 | 24 | 20 | 31 |
| 2 | 37 | 34 | 29 | 42 |
| 3 | 44 | 42 | 37 | 49 |
| 4 | 56 | 51 | 43 | 62 |
| 5 | 64 | 59 | 50 | 71 |
| 6 | 71 | 65 | 56 | 77 |
| 7 | 75 | 69 | 61 | 82 |
| 8 | 80 | 73 | 65 | 86 |

The results summarized in Tables VIII and IX indicate that carbomer is able to retard sodium valproate release from the tablets, providing sustained release properties.

Therefore, sodium valproate release kinetics from the tablets can be controlled by changing the carbomer concentration in the tablet composition. Specifically, increasing carbomer concentration in the tablets decreases sodium valproate release rate.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A process for preparing a pharmaceutical composition comprising as an active ingredient a hygroscopic salt of valproic acid, comprising the step of intimately mixing (i) said hygroscopic salt; (ii) a carbomer and (iii) a non-hygroscopic additive to form a homogeneous mixture; wherein the amount of said carbomer and said non-hygroscopic additive are sufficient relative to the amount of said hygroscopic salt to produce said mixture having the following property: when compressed into tablets, said tablets do not absorb more than 5% water by weight when tested after being stored for 3 months at 75% relative humidity; wherein said pharmaceutical composition is free of valproic acid; and wherein the weight ratio of carbomer to the hygroscopic salt of valproic acid ranges from about 1:3 to about 1:100.

2. The process of claim 1, wherein said hygroscopic salt of valproic acid is sodium valproate.

3. The process of claim 1, wherein the weight ratio of carbomer to the hygroscopic salt of valproic acid ranges from about 1:3 to about 1:10.

4. The process of claim 1, wherein the weight ratio of non-hygroscopic additive to the hygroscopic salt of valproic acid ranges from about 1:6 to about 1:2.

5. The process of claim 1, further comprising a step of adding at least one excipient to the mixture of said hygroscopic salt, said carbomer and said non-hygroscopic additive.

6. The process of claim 1, further comprising a step of directly compressing said non-hygroscopic composition into a solid dosage form.

7. The process of claim 6, wherein said solid dosage form contains from about 50 to about 1200 mg of sodium valproate.

8. The process of claim 7, wherein said solid dosage form contains from about 6 mg to about 400 mg of carbomer.

9. The process of claim 8, wherein, said solid dosage form contains from about 90 mg to about 400 mg of non-hygroscopic additive.

10. The process of claim 1, wherein said non-hygroscopic additive is selected from the group consisting of dibasic calcium phosphate anhydrous, calcium silicate, microcrystalline cellulose and mixtures thereof.

11. The process of claim 1, wherein said non-hygroscopic additive is present in an amount such that the weight ratio of non-hygroscopic additive to the hygroscopic salt of valproic acid is in the range of from about 1:6 to 1:2.

12. The process of claim 5, wherein said excipient is selected from the group consisting of lubricants, disintegrators, glidants, adsorbents, and mixtures thereof.

13. The process of claim 12, wherein said lubricant is selected from the group consisting of stearic acid, a salt of stearic acid, talc, sodium lauryl sulfate, sodium stearyl fumarate and mixtures thereof.

14. The process of claim 13, wherein said lubricant is present in an amount of from about 0.25% to about 5% of the weight of the final composition.

15. The process of claim 12, wherein said disintegrator is selected from the group consisting of crosscarmelose sodium, sodium starch glycolate, starch, magnesium aluminum silicate, colloidal silicon dioxide, carboxymethyl cellulose, microcrystalline cellulose, and mixtures thereof.

16. The process of claim 15, wherein said disintegrator is present in an amount of from about 0.5% to about 25% of the weight of the final composition.

17. The process of claim 12, wherein said glidant is selected from the group consisting of colloidal silicon dioxide, talc and mixtures thereof.

18. The process of claim 17, wherein said glidant is present in an amount of from about 0.1% to about 10% of the weight of the final composition.

19. The process of claim 12, wherein said adsorbent is selected from the group consisting of colloidal silicon dioxide, microcrystalline cellulose, calcium silicate and mixtures thereof.

20. The process of claim 19, wherein said adsorbent is present in an amount of from about 0.05% to about 42% of the weight of the final composition.

21. The process of claim 6, wherein said solid dosage form is selected from the group consisting of a tablet, a caplet, a pellet, a capsule, a tablet which disintegrates into granules, and a pill.

22. The process of claim 21, wherein the tablet is an enteric coated tablet.

23. The process of claim 21, wherein the tablet is coated with an anti-moisture barrier.

24. The process of claim 1, wherein said mixing is carried out in conditions of relative humidity of greater than 30%.

25. A non-hygroscopic oral pharmaceutical composition comprising a pharmaceutically effective amount of a hygroscopic salt of valproic acid, a carbomer, and a non-hygroscopic additive, wherein the amount of said carbomer and said non-hygroscopic additive are sufficient relative to the amount of said hygroscopic salt to produce said composition having the following property: not absorbing more than 5% by weight water when tested after being stored for 3 months at 75% relative humidity; wherein said pharmaceutical composition is free of valproic acid; and wherein the weight ratio of carbomer to the hygroscopic salt of valproic acid ranges from about 1:3 to about 1:100.

26. A non-hygroscopic oral pharmaceutical composition comprising a pharmaceutically effective amount of a hygroscopic salt of valproic acid, a carbomer, and a non-hygroscopic additive, wherein the amount of said carbomer and said non-hygroscopic additive are sufficient relative to the amount of said hygroscopic salt to produce said composition having the following property: when compressed into tablets, said tablets do not absorb more than 5% by weight water when tested after being stored for 3 months at 75% relative humidity; wherein said pharmaceutical composition is free of valproic acid; and wherein the weight ratio of carbomer to the hygroscopic salt of valproic acid ranges from about 1:3 to about 1:100.

27. The pharmaceutical composition of claim 26, wherein said hygroscopic salt of valproic acid is sodium valproate.

28. The pharmaceutical composition of claim 26, wherein the weight ratio of carbomer to the hygroscopic salt of valproic acid ranges from about 1:3 to about 1:10.

29. The pharmaceutical composition of claim 26, wherein the non-hygroscopic additive is present in an amount such that the weight ratio of non-hygroscopic additive to the hygroscopic salt of valproic acid is in the range of from about 1:6 to about 1:2.

30. The pharmaceutical compostion of claim 29, wherein said non-hygroscopic additive is present in an amount such that the weight ratio of the non-hygroscopic additive to the carbomer is in the range of from about 2:1 to about 35:1.

31. The pharmaceutical composition of claim 26, further comprising at least one excipient.

32. The pharmaceutical composition of claim 26, wherein the composition contains from about 50 to about 1200 mg of sodium valproate.

33. The pharmaceutical composition of claim 32, wherein the composition contains from about 6 mg to about 400 mg of carbomer.

34. The pharmaceutical composition of claim 33, wherein the composition contains from about 90 mg to about 400 mg of non-hygroscopic additive.

35. The pharmaceutical composition of claim 26, wherein said non-hygroscopic additive is selected from the group consisting of dibasic calcium phosphate anhydrous, calcium silicate, microcrystalline cellulose and mixtures thereof.

36. The pharmaceutical composition of claim 26, further comprising an excipient selected from the group consisting of lubricants, disintegrators, glidants, adsorbents, and mixtures thereof.

37. The pharmaceutical composition of claim 36 wherein said lubricant is selected from the group consisting of stearic acid, a salt of stearic acid, talc, sodium lauryl sulfate, sodium stearyl fumarate and mixtures thereof.

38. The pharmaceutical composition of claim 37, wherein said lubricant is present in an amount of from out 0.25% to about 5% of the weight of the final composition.

39. The pharmaceutical composition of claim 36, wherein said disintegrator is selected from the group consisting of crosscarmelose sodium, sodium starch glycolate, starch, magnesium aluminum silicate, colloidal silicon dioxide, carboxymethyl cellulose, microcrystalline cellulose, and mixtures thereof.

40. The pharmaceutical composition of claim 39, wherein said disintegrator is present in an amount of from about 0.5% to about 25% of the weight of the final composition.

41. The pharmaceutical composition of claim 36, wherein said glidant is selected from the group consisting of colloidal silicon dioxide, talc and mixtures thereof.

42. The pharmaceutical composition of claim 41, wherein said glidant is present in an amount of from about 0.1% to about 10% of the weight of the final composition.

43. The pharmaceutical composition of claim 36, wherein said adsorbent is selected from the group consisting of colloidal silicon dioxide, microcrystalline cellulose, calcium silicate and mixtures thereof.

44. The pharmaceutical composition of claim 43, wherein said adsorbent is present in an amount of from about 0.05% to about 42% of the weight of the final composition.

45. The pharmaceutical composition of claim 26, wherein the non-hygroscopic oral pharmaceutical composition is a tablet, a caplet, a pellet, a capsule, a tablet which disintegrates into granules, and a pill.

46. The pharmaceutical composition of claim 45, wherein the tablet is an enteric coated tablet.

47. The pharmaceutical composition of claim 46, wherein the tablet is coated with an anti-moisture barrier.

48. The pharmaceutical composition of claim 26, wherein the non-hygroscopic oral pharmaceutical composition is a sustained release tablet.

49. The pharmaceutical composition of claim 48, wherein the weight ratio of carbomer to the hygroscopic salt of valproic acid ranges from about 1:6 to about 1:20.

50. A method of treating a medical condition in a human patient, the method comprising the step of orally administering a non-hygroscopic pharmaceutical composition for release of a salt of valproic acid into the bloodstream at a physiologically effective level, wherein said composition comprises a pharmaceutically effective amount of a hygroscopic salt of valproic acid, a carbomer, and a non-hygroscopic additive, and wherein the weight ratio of the carbomer to the hygroscopic salt of valproic acid is from about 1:3 to about 1:100 and the weight ratio of the non-hygroscopic additive to the hygroscopic salt of valproic acid is from about 1:6 to about 1:2; wherein said pharmaceutical composition is free of valproic acid; and wherein said medical condition is epilepsy.

51. A method of treating a medical condition in a human patient, the method comprising the step of orally administering a non-hygroscopic pharmaceutical composition for release of a salt of valproic acid into the bloodstream at a physiologically effective level, wherein said composition comprises a pharmaceutically effective amount of a hygroscopic salt of valproic acid, a carbomer, and a non-hygroscopic additive, and wherein the weight ratio of the carbomer to the hygroscopic salt of valproic acid is from about 1:3 to about 1:100 and the weight ratio of the non-hygroscopic additive to the hygroscopic salt of valproic acid is from about 1:6 to about 1:2; wherein said pharmaceutical composition is free of valproic acid; and wherein said medical condition is a psychotic disorder.

52. A method of treating a medical condition in a human patient, the method comprising the step of orally administering a non-hygroscopic pharmaceutical composition for release of a salt of valproic acid into the bloodstream at a physiologically effective level, wherein said composition comprises a pharmaceutically effective amount of a hygroscopic salt of valproic acid, a carbomer, and a non-hygroscopic additive, and wherein the weight ratio of the carbomer to the hygroscopic salt of valproic acid is from about 1:3 to about 1:100 and the weight ratio of the non-hygroscopic additive to the hygroscopic salt of valproic acid is from about 1:6 to about 1:2; wherein said medical condition is a migraine headache.

53. The method of claim 1 wherein the weight ratio of the carbomer to the hygroscopic salt of valproic acid ranges from about 1:3 to about 1:100, and the weight ratio of the non-hygroscopic additive to the hygroscopic salt of valproic acid ranges from about 1:6 to about 1:2.

54. The method of claim 53 further comprising a step of directly compressing the composition into a solid dosage form.

55. The composition of claim 26, said composition having been formed into a solid dosage form by direct compression.

* * * * *